(12) United States Patent
Eisenberg et al.

(10) Patent No.: US 9,463,195 B2
(45) Date of Patent: Oct. 11, 2016

(54) DISSOLUTION OF AMYLOID FIBRILS BY FLAVONOIDS AND OTHER COMPOUNDS

(75) Inventors: David S. Eisenberg, Los Angeles, CA (US); Melinda Balbirnie, Santa Monica, CA (US)

(73) Assignee: The Regents of the University of California, Oakland, CA (US)

(*) Notice: Subject to any disclaimer, the term of this patent is extended or adjusted under 35 U.S.C. 154(b) by 1878 days.

(21) Appl. No.: 12/519,058

(22) PCT Filed: Dec. 14, 2007

(86) PCT No.: PCT/US2007/025594
§ 371 (c)(1),
(2), (4) Date: Jun. 12, 2009

(87) PCT Pub. No.: WO2008/076351
PCT Pub. Date: Jun. 26, 2008

(65) Prior Publication Data
US 2010/0048510 A1    Feb. 25, 2010

Related U.S. Application Data

(60) Provisional application No. 60/874,950, filed on Dec. 15, 2006.

(51) Int. Cl.
*A61M 1/14* (2006.01)
*A61M 1/34* (2006.01)
*A61K 31/65* (2006.01)
*A61M 1/30* (2006.01)

(52) U.S. Cl.
CPC ............... *A61K 31/65* (2013.01); *A61M 1/30* (2013.01); *A61M 1/3486* (2014.02)

(58) Field of Classification Search
CPC .......................... A61M 1/30; A61M 1/3486
USPC ........................................................ 514/82
See application file for complete search history.

(56) References Cited

U.S. PATENT DOCUMENTS

2005/0031651 A1* 2/2005 Gervais et al. ............... 424/400

OTHER PUBLICATIONS

Yamamoto et al. (Historical background and clinical treatment of dialysis-related amyloidosis, Biochimica et Biophysica Acta 1753 (2005) 4-10.*
Hudson et al. FEBS Journal, 2009, vol. 276, pp. 5960-5972.*
Azuma et al. Acta Neurologica Scandinavica, 1991, vol. 84, No. 1, pp. 46-50 (Abstract attached).*
Forssell et al. Acta Neurologica Scandinavica Supplementum, 1989, vol. 79, No. 121, pp. 43-66 (Abstract attached).*
Abe et al. (2003). Effect of beta(2)-microglobulin adsorption column on dialysis-related amyloidosis. Kidney Int. 64(4):1522-8.
Ayli et al. (2005).The effect of high-flux hemodialysis on dialysis-associated amyloidosis. Ren Fail. 27(1): 31-4.
Bastianetto et al. (2006) Neuroprotective effects of green and black teas and their catechin gallate esters against beta-amyloid-induced toxicity. Eur J Neurosci. 23(1):55-64.
Bush, A.I. (2002) Metal complexing agents as therapies for Alzheimer's disease. Neurobiol. Aging. 23(6): 1031-8.
Chow et al. (2001) Phase I pharmacokinetic study of tea polyphenols following single-dose administration of epigallocatechin gallate and polyphenon E. Cancer Epidemiol Biomark Prev. 10:53-58.
Gordon et al. (2007). Intravenous levodopa administration in humans based on a two-compartment kinetic model. J Neurosci Methods. 159:300-307.
Ivanova et al. (2004). An amyloid-forming segment of beta2-microglobulin suggests a molecular model for the fibril. Proc Natl Acad Sci. 101(29): 10584-9.
Jadoul. (1998). Dialysis-related amyloidosis: importance of biocompatibility and age. Nephrol Dial Transplant. 13(Supp 7): 61-64.
Kocisko et al. (2003). New inhibitors of scrapie-associated prion protein formation in a library of 2,000 drugs and natural products. J Virology. 77: 10288-10294.
Kuriyama et al. (2006). Green tea consumption and cognitive function: a cross-sectional study from the Tsurugaya Project. Am J Clin Nutr. 83(2):355-61.
LeVine III. (1999). Quantification of beta-sheet amyloid fibril structures with thioflavin T. Methods Enzymol. 309: 274-84.
Nakagawa, K., Miyazawa T. (1997) Chemiluminescence-high-performance liquid chromatographic determination of tea catechin, (−)-Epigallocatechin 3-Gallate, at Picomole Levels in rat and human plasma. Anal Biochem. 248:41-49.
Nakagawa et al. (1997) Dose-dependent incorporation of tea catechins, (−)-Epigallocatechin-3-gallate and (−)-Epigallocatechin, into Human Plasma. Biosci Biotechnol Biochem. 61(12):1981-1985.
Ono et al. (2005). Preformed beta-amyloid fibrils are destabilized by coenzyme Q10 in vitro. Biochem Biophys Res Commun. 330(1):111-116.
Pepys. (2006). Amyloidosis. Annu Rev Med. 57: 223-241.
Tsuruoka et al. (2004). Beta2-microglobulin adsorption column reduces digoxin trough level during hemodialysis: three case reports. Ther Drug Monit. 26(4): 450-452.
Ullmann et al. (2004). Plasma-kinetic characteristics of purified and isolated grean tea catechin epigallocatechin gallate (EGCG) after 10 days repeated dosing in healthy volunteers. Int J Vitam Nutr Res. 74(4):269-278.
Unno et al. (1996). Analysis of (−)-Epigallocatechin gallate in human serum obtained after ingesting green tea. Biosci. Biotechnol. Biochem. 60(12):2066-2068.
Weissmann C., Aguzzi A. (2005) Approaches to therapy of prion diseases. Ann Rev Med. 56:321-344.
Winchester, J. F., J. A. Salsberg, et al. (2003). "Beta-2 microglobulin in ESRD: an in—depth review." Adv Ren Replace Ther 10(4): 279-309.
Yamamoto, S. and F. Gejyo (2005). "Historical background and clinical treatment of dialysis-related amyloidosis." Biochim Biophys Acta 1753(1): 4-10.

* cited by examiner

*Primary Examiner* — James D Anderson
(74) *Attorney, Agent, or Firm* — Gates & Cooper LLP

(57) ABSTRACT

Methods for disrupting amyloid fibrils in a subject, comprising combining an effective amount of a β-2 microglobulin fibril disrupting compound with a medium associated with the subject, are disclosed. The invention also relates to combining the β-2 microglobulin fibril disrupting compound ex vivo with the blood during dialysis treatment of an animal. It also relates to methods for determining which compounds are effective at disrupting amyloid fibrils in a medium.

16 Claims, 18 Drawing Sheets

DISSOLUTION OF AMYLOID FIBRILS BY FLAVONOIDS AND OTHER COMPOUNDS

CROSS REFERENCE TO RELATED APPLICATIONS

This application is a National Stage entry under 35 U.S.C. §371 of Application No. PCT/US2007/025594, filed Dec. 14, 2007, which claims the benefit of U.S. Application No. 60/874,950, filed Dec. 15, 2006. Each of these applications is incorporated by reference in its entirety and for all purposes.

This invention was made with Government support of Grant No. GM31299, awarded by the National Institute of Health. The Government has certain rights in this invention.

BACKGROUND OF THE INVENTION

Amyloid formation plays a central role in over 20 human diseases, for example, Alzheimer's disease, type II diabetes, and the systemic amyloidoses (for review, see Pepys, M B *Annu. Rev. Med.* 2006. 57:8.1-8.19). It occurs when a normally soluble protein is extracellularly deposited as fibrils with characteristic properties (long, unbranched fibrils producing a cross-beta X-ray diffraction pattern and binding the dyes Congo red and Thioflavin T). The 20-odd proteins known to reassemble in this surprisingly similar manner share no apparent sequence, structural, or functional similarity in their native states.

$\beta$-2 microglobulin (also referred to herein as B2M or $\beta$-2M) is the ~12 kDa subunit of the cell-surface MHC Class I complex and is normally found at circulating concentrations of 1-2 mg/L. When a patient's kidneys fail, such as for patients undergoing kidney dialysis, the kidneys are unable to effectively filter and catabolize the $\beta$-2 microglobulin and its circulating concentrations can soar to as high as 50-70 mg/L (Pepys, M B *Annu. Rev. Med.* 2006. 57:8.1-8.19).

Over 300,000 people in the United States and over 1 million worldwide are on kidney or peritoneal dialysis. (*United States Renal Data System, USRDS* 2005 *Annual Data Report: Atlas of End-Stage Renal Disease in the United States National Institutes of Health, National Institute of Diabetes and Digestive and Kidney Diseases*, Bethesda, Md., 2005).

After about 5 years on dialysis, $\beta$-2 microglobulin may deposit as amyloid fibrils, primarily in the joints of patients as amyloid in a painful condition known as dialysis-related amyloidosis (herein, DRA) (Yamamoto, S. and F. Gejyo (2005). "Historical background and clinical treatment of dialysis-related amyloidosis." *Biochim Biophys Acta* 1753 (1): 4-10), which is a form of systemic amyloidosis. DRA often presents as carpal tunnel syndrome with or without other destructive arthropathies and can be detected by MRI. One-third of the patients on hemodialysis will develop dialysis-related amyloidosis within 4 years; after 7 years, more than 90% will be affected, and by 15 years on hemodialysis, all patients will have DRA (Jadoul, M. (1998). "Dialysis-related amyloidosis: importance of biocompatibility and age." *Nephrol Dial Transplant* 13 Supp 7: 61-4). Thus, DRA eventually affects all long-term kidney dialysis patients. If left untreated, the systemic amyloidosis can be deadly. Amyloid deposits may develop in the heart and kill the patient.

High-flux dialysis membranes used during dialysis have improved $\beta$-2 microglobulin filtration, but have not eliminated DRA (Ayli, M., D. Ayli, et al. (2005). "The effect of high-flux hemodialysis on dialysis-associated amyloidosis." *Ren Fail* 27(1): 31-4). Additionally, B2M adsorption columns have been used in conjunction with high-flux dialysis membranes with some improvement in DRA patients (Abe, T., K. Uchita, et al. (2003). "Effect of beta(2)-microglobulin adsorption column on dialysis-related amyloidosis." *Kidney Int* 64(4): 1522-8; Winchester, J. F., J. A. Salsberg, et al. (2003). "Beta-2 microglobulin in ESRD: an in-depth review." *Adv Ren Replace Ther* 10(4): 279-309). However, these columns are not highly specific for B2M and can have deleterious effects (Tsuruoka, S., M. Wakaumi, et al. (2004). "Beta2-microglobulin adsorption column reduces digoxin trough level during hemodialysis: three case reports." *Ther Drug Monit* 26(4): 450-2). Currently the only effective means of combating the amyloidosis is kidney transplantation. See "Beta-2 microglobulin in ESRD: an in-depth review" Winchester et al., *Adv in Renal Replacement Ther* (2003) Vol. 10(4): 279-309; "Historical background and clinical treatment of dialysis-related amyloidosis" Yamamoto et al., *Biochim Biophys Acta* (2005) November 10;1753(1):4- 10.

Disrupting the $\beta$-2 microglobulin fibrils has potential therapeutic application in treating DRA. A compound that could disrupt these preformed aggregates could potentially remedy the amyloidosis and delay or eliminate the need for transplantation. Therefore, there is a need for compounds that can disrupt $\beta$-2 microglobulin fibrils.

DESCRIPTION

Figure 1:
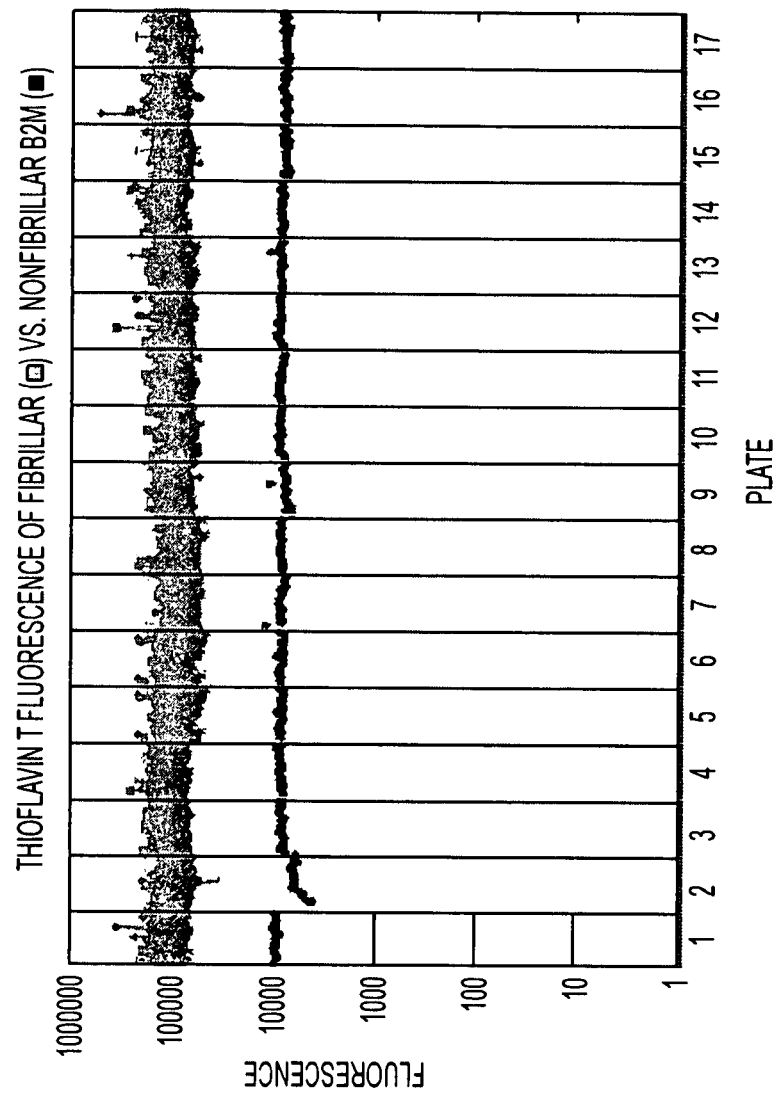
FIG. 1 is a graph depicting the fluorescence of thioflavin T (also referred to herein as ThT) for each well in each plate. In every 384-well plate, preformed B2M fibrils were distributed among all but 16 wells. The remaining 16 wells contain nonfibrillar B2M. The initial thioflavin T fluorescence of all wells is shown in the chart. Fibrillar and nonfibrillar samples are clearly distinguishable by their fluorescence and are separated by a factor of 10 in fluorescence intensity. No compound has been added to any of the wells.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Through the experiments described in the Examples below, we have found that, among others, epigallocatechin gallate (herein, EGCG), the major flavonoid component of green tea extract, disrupts preformed human β-2 microglobulin fibrils. This finding shows that EGCG, among others, may be of use in the treatment of dialysis-related amyloidosis, which involves deposition of β-2 microglobulin fibrils in the joints, and is currently remedied only by kidney transplantation.

An embodiment of the invention includes gallate and epigallocatechin compounds, their pharmaceutically acceptable salts, and their derivatives. Examples of epigallocatechin gallate derivatives which have been tested and found to decrease the fluorescence, exhibiting slopes in the range from −0.06 to −0.07, include pyrogallin, 7-deshydroxypyrogallin-4-carboxylic acid, and methyl 7-deshydroxypyrogallin-4-carboxylate, purpurogallin, and theaflavin. Examples of other gallate and epigallocatechin compounds and their derivatives include epigallocatechin, epigallocatechin 3,5-digallate, 2',2'-bisepigallocatechin digallate, epicatechin monogallate, epicatechin, epicatechin pentaacetate, catechin pentaacetate, and catechin pentabenzoate. Two related compounds that are not derivatives of a gallate or epigallocatechin compound but which were also effective in the fluorescence assay at disrupting β-2 microglobulin fibers are eveminic acid and methyleverninic acid; these compounds had a slope assay score in the range of −0.06 to −0.07.

As used herein, "slope assay score" means the slope of the relative fluorescence of thioflavin T versus time curve for a given compound in a thioflavin T fluorescence assay. A negative slope signifies a decrease in thioflavin T fluorescence over time. A slope assay score of, for example, about −0.06 or lower is indicative of effectiveness at disrupting β-2 microglobulin fibrils. As used in the context of slope assay score, "lower" means having a greater negative value; for example, −0.07 has a greater negative value, and is thus lower, than −0.06, indicating a greater disrupting activity.

Other compounds that have been shown to be effective in the fluorescence assay at disrupting β-2 microglobulin fibers include stictic acid, haematommic acid, meclocycline sulfosalicylate, dobutamine, apomorphine, primaquine diphosphate, protoporphyrin IX, nalidixic acid, leoidin, dimenhydrinate, carminic acid, oxidopamine, dequalinium dichloride, and econazole nitrate, as well as pharmaceutically acceptable salts or derivatives thereof.

Compounds, such as the above, that disrupt β-2 microglobulin fibrils, as shown by, for example, electron microscopy and/or a decreased thioflavin T/β-2 microglobulin fibril fluorescence (where the decrease is not due to quenching), as well as pharmaceutically acceptable salts or derivatives thereof, are collectively referred to herein as "β-2 microglobulin fibril disrupting compounds." As used herein, "quench" means causing a decrease in fluorescence for reasons not associated with fibril disruption. As used herein, "normalize" means adjusting data to a common scale, for example in such a way as to remove errors, including, for example, errors caused by fluorescence quenching. Compounds that cause fluorescence quenching generally drop the fluorescence quickly, fibril disruptors do not. Fluorescence quenching compounds are mainly eliminated from the analysis by removing data from the first hour after mixing. Thus, a compound that reduces fluorescence not due to quenching is a β-2 microglobulin fibril disrupting compound, as may be verified by measuring the slope assay score for the compound as well as by electron microscopy. Such compounds fall into several chemical groups, but share certain steric characteristics (e.g., planarity) in addition to their measurable characteristics in fluorescence and electron microscopy. These groups include catechol-like, salicylate-like, and tetracycline-like compounds.

As used herein, the term "catechol-like compounds" includes, for example, epigallocatechin gallate, benserazide hydrochloride, purpurogallin, carminic acid, oxidopamine, theaflavin, apomorphine hydrochloride, dobutamine hydrochloride, and analogues thereof. It also includes, for example, other compounds with substituents similar in structure to catechol and having the indicated activity.

As used herein, the term "salicylate-like compounds" includes, for example, meclocycline sulfosalicylate, haematommic acid, carminic acid, eveminic acid, and analogues thereof. It also includes, for example, other compounds with substituents similar in structure to salicylic acid and having the indicated activity.

As used herein, the term "tetracycline-like compounds" includes, for example, meclocycline sulfosalicylate, minocycline, chlorotetracycline, and oxytetracycline, and analogues thereof. It also includes, for example, other compounds with substituents similar in structure to tetracycline and having the indicated activity.

As used herein, the term "β-2 microglobulin fibrils" includes, for example, fibrils formed from β-2 microglobulin protein having an amino acid sequence according to any of its various polymorphic forms. It also includes any variations in the fibrils' tertiary or quaternary structure, for example, having 2, 3, 4 or more strands, and it also includes fibrils with complexes of β-2 microglobulin and other proteins. It also includes fibrils formed according to the procedure discussed in Ivanova et al. See Ivanova et al. (*Proc Natl Acad Sci U.S.A.* 2004 July 20; 101(29):10584-9).

As used herein, "disrupt" means, for example, causing or bringing about the dissociation of fibrils into smaller units, including dissociation into β-2 microglobulin monomers, and dissolution of the protein or fibrils.

A further embodiment of the invention includes a method for disrupting amyloid fibrils in a subject, comprising combining a β-2 microglobulin fibril disrupting compound with a medium associated with the subject. As used herein, "medium associated with a subject" includes, for example, blood, including human blood, whether within the subject's body or outside of it, including, for example, blood temporarily removed from a subject's body during dialysis, or blood within a tissue.

The methods and other embodiments of this invention can be calibrated so as to be effective against any polymorphism of amyloid fibrils, including polymorphisms of β-2 microglobulin fibrils.

The following compounds produced a dose-dependent effect on thioflavin T/β-2 microglobulin fibril fluorescence: stictic acid (Gaia Chemical Corp D7000); haematommic acid (Microsource Discovery Systems, Inc. Spectrum Collection); meclocycline sulfosalicylate (SIGMA M1388); apomorphine hydrochloride (SIGMA A4393); primaquine diphosphate (SIGMA 160393); and dobutamine hydrochloride (SIGMA D0676). Compounds of the invention, including stictic acid, haematommic acid, and meclocycline sulfosalicylate also visibly disrupted the β2M fibrils (by EM) at the concentrations tested.

Epigallocatechin gallate (herein, "Compound 22"; SIGMA product number E4143) and benserazide hydrochloride (herein, "Compound L18"; SIGMA product number B7283), among others, disrupt human β-2 microglobulin fibrils in a dose-dependent manner and at concentrations that are clinically achievable. Both of these compounds have completed the safety phase of clinical trials for other diseases and could be readily administered during dialysis. The structures of Compound 22 and Compound L18 are presented below. Referred to in this text as Compound 21 is Polyphenon 60, a green tea extract; compound 22 is the most abundant component of Compound 21.

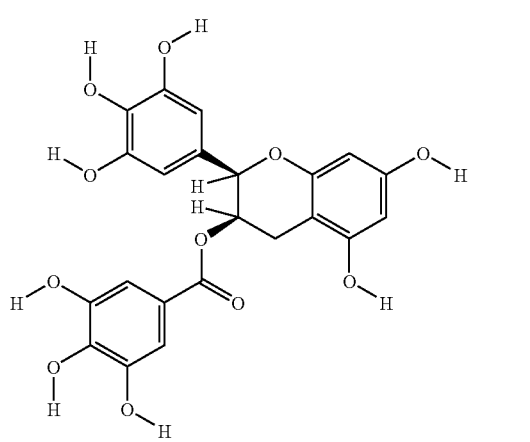 [SMILES: O=C(O[C@@H]1Cc2c(O)cc(O)cc2O[C@@H]1c1cc(O)c(O)c(O)c1)c1cc(O)c(O)c(O)c1]

Compound 22

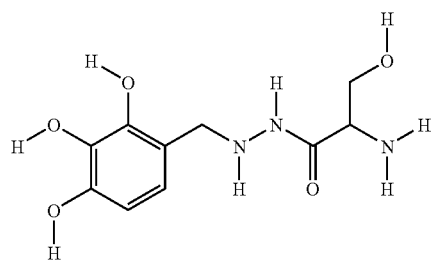

Compound L18

Use of Flavonoids and other Compounds in Dialysis Therapy

Compounds 22 and L18 have both been through phase III clinical trials for unrelated diseases, so their safety and toxicology profiles are well established. Compounds 22 and L18, among others, disrupt preformed human B2M fibrils in the range of 10 μM concentration. This effective concentration can be achieved in plasma. For example, concentrations as high as 10 μM can be obtained in rats following a single injection, for other purposes (Nakagawa, K., Miyazawa T. *Anal Biochem.* 1997. 248, 41-49).

In one pharmacokinetic study, patients had an average plasma level of 1 μM following a single oral dose of Compound 22 (Chow, H. H. S., Cai, Y., Alberts, D. S., Hakim, I. et al. *Cancer Epidemiol. Biomark. Prev.* 2001, 10, 53-58). In another study, human plasma levels reached 2-4 μM of Compound 22 following a single oral dose (Unno, T., Kondo, K., Itakura, H., Takeo, T. *Biosci. Biotechnol. Biochem.* 1996, 60, 2066-68). And in yet another study plasma levels reached 4.4 μM of Compound 22 following a single oral dose (Nakagawa, Okuda and Miyazawa *Biosci Biotechnol Biochem* 1997 December; 61(12):1981-5. Compound 22 is known to be well-tolerated orally at doses at least twice this high (Ullmann, Haller et al. 2004). Plasma concentrations of 6 μM Compound L18 are routinely achievable (Gordon M et al 2006 Aug. 23 J Neurosci Methods Epub ahead of print). Because the invention involves administering Compounds 22 and L18 directly into the bloodstream during dialysis, we can achieve a concentration that is clinically relevant to the disease, such as 10 μM.

At least one compound that reverses amyloid fibrillar structure is already being used in patients for other purposes. Clioquinol is a copper chelator that disrupts preformed β-amyloid fibrils. See Bush, A. I. *Neurobiol. Aging* 2002 23(6): 1031-8. The safety of this compound is already established in humans. The Bush study shows that the compound is effective in mice. Because it is also an FDA-approved antibiotic, it was readily transferable to Alzheimer's disease patients.

Other compounds chemically and structurally related to Compounds 22 and L18 can be tested, for example, catechins, flavonoids, polyphenols, and antioxidants, and can be verified using a focused library of compounds and conducting fluorescence and electron microscopy assays. EGCG and other compounds that act as fibril disruptors can be used on other amyloid-forming proteins and peptides. In vivo assays can be conducted.

Figure 5:
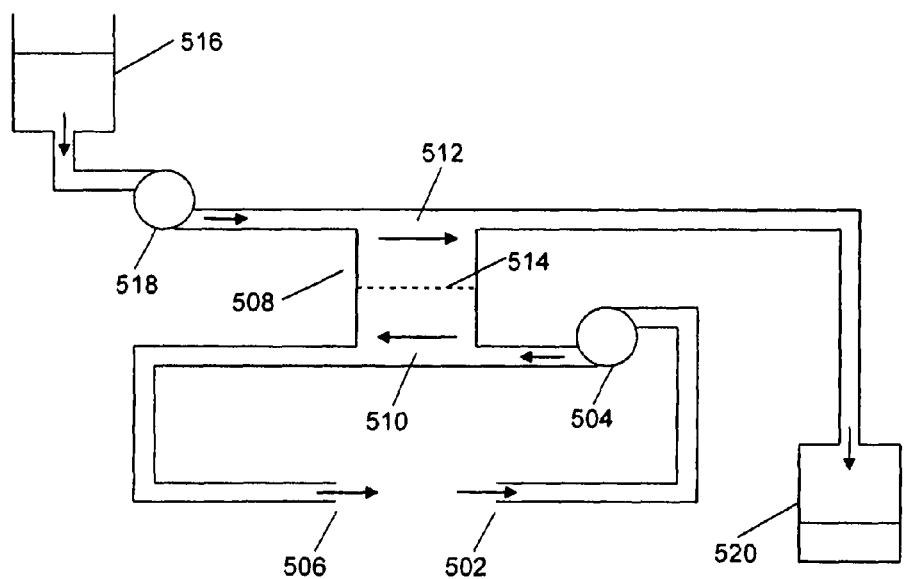
FIG. 5 is a block diagram of a kidney dialysis machine.
Figure 6:
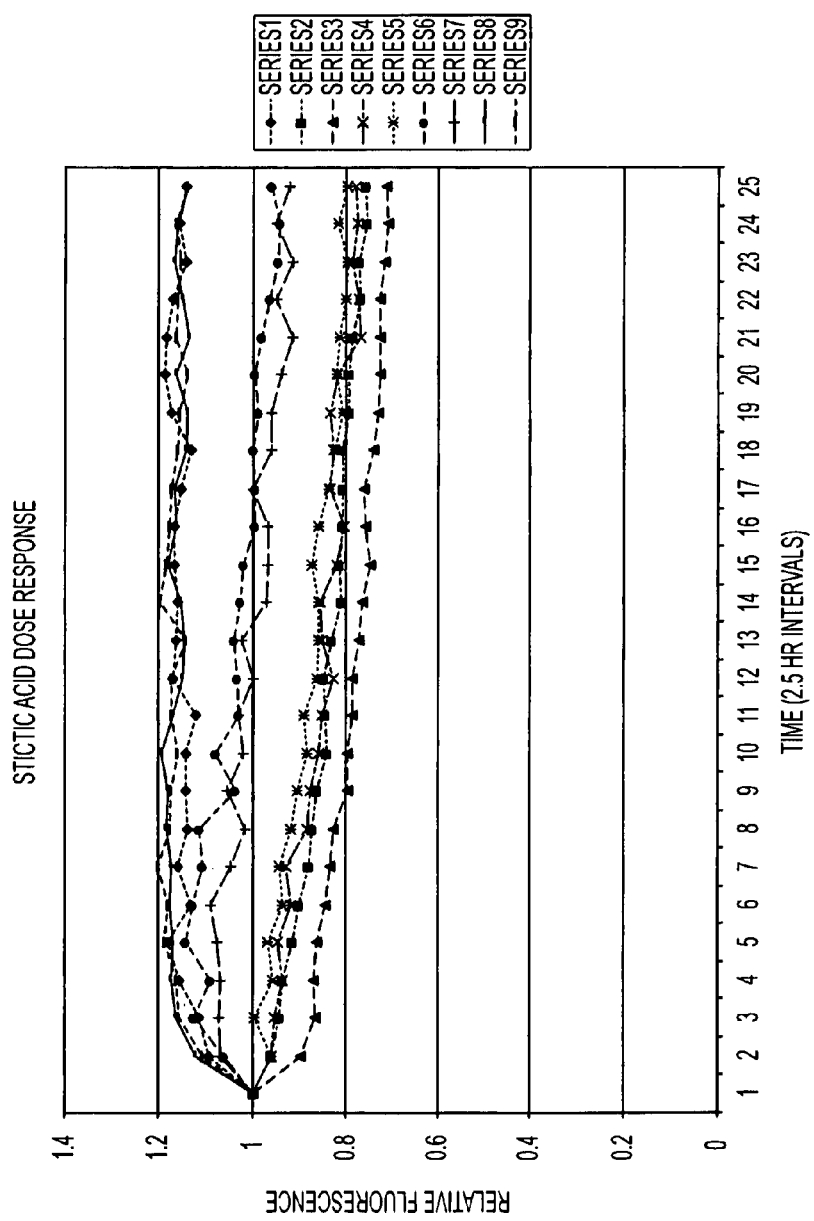
FIG. 6 is a graph depicting the effect of stictic acid on the thioflavin T/β-2M fibril fluorescence as a function of time. Stictic acid affects the thioflavin T/β-2M fibril fluorescence in a dose-dependent manner at concentrations as low as 10 µM and possibly lower (note that the dose dependency was not tested between 1 and 10 µM and there may be an effect at less than 10 µM). Series 1 is a control (human β-2M fibrils+thioflavin T in 1% DMSO). Series 2 and 3 are duplicate wells of human β-2M fibrils+thioflavin T+1 mM stictic acid (final concentration in the well). Series 4 and 5 are duplicates of human β-2M fibrils+thioflavin T+100 µM stictic acid. Series 6 and 7 are duplicates of human β-2M fibrils+thioflavin T+10 µM stictic acid. Series 8 and 9 are duplicates of human β-2M fibrils+thioflavin T+1 µM stictic acid.
Figure 7:
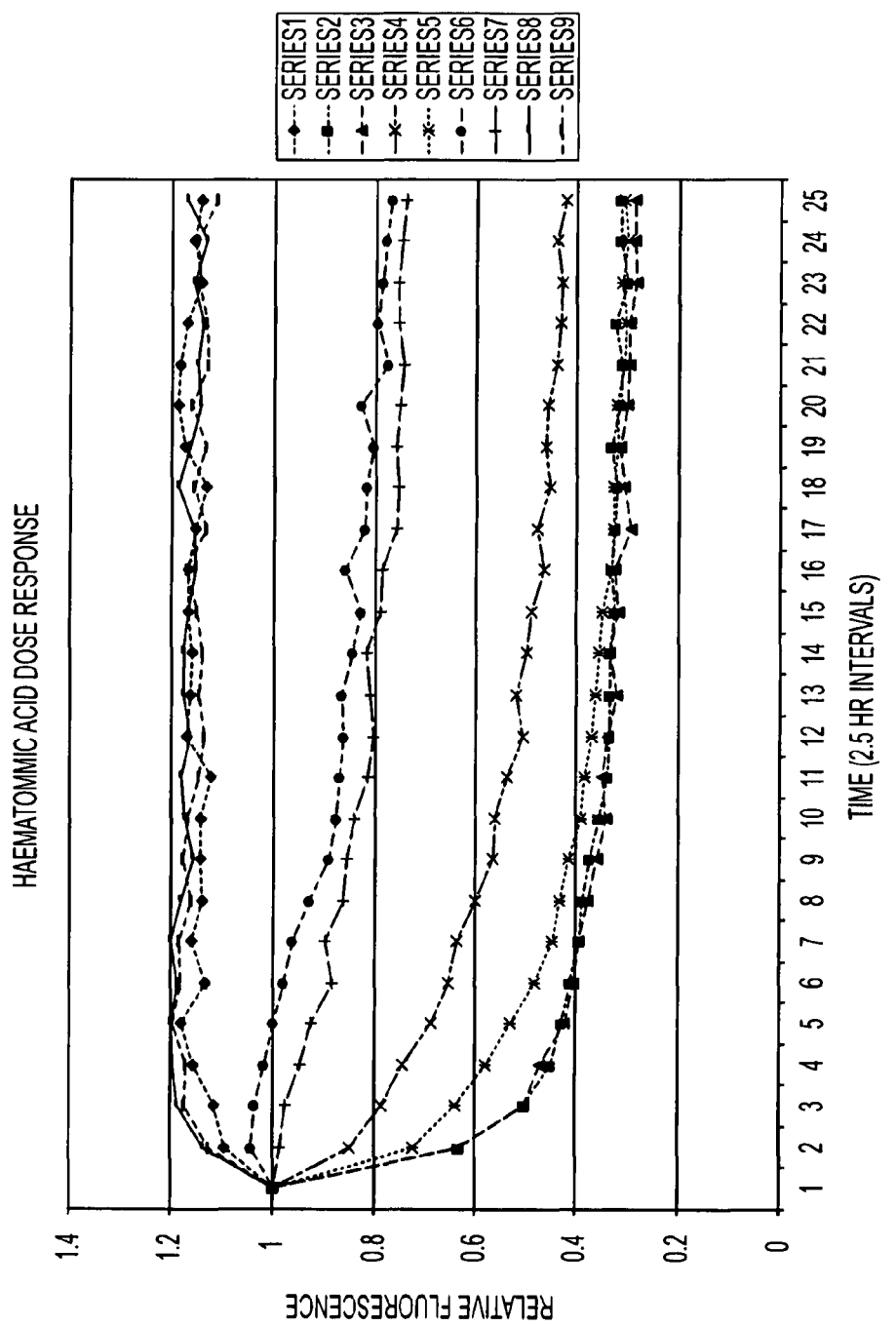
FIG. 7 is a graph depicting the effect of haematommic acid on the thioflavin T/β-2M fibril fluorescence as a function of time. Haematommic acid affects the thioflavin T/β-2M fibril fluorescence in a dose-dependent manner at concentrations less than or equal to 10 µM. Series 1 is a control (human β-2M fibrils+thioflavin T in 1% DMSO). Series 2 and 3 are duplicates of human β-2M fibrils+thioflavin T+1 mM haematommic acid (final concentration). Series 4 and 5 are duplicates of human β-2M fibrils+thioflavin T+100 µM haematommic acid. Series 6 and 7 are duplicates of human β-2M fibrils+thioflavin T+10 µM haematommic acid. Series 8 and 9 are duplicates of human β-2M fibrils+thioflavin T+1 µM haematommic acid.
Figure 8:
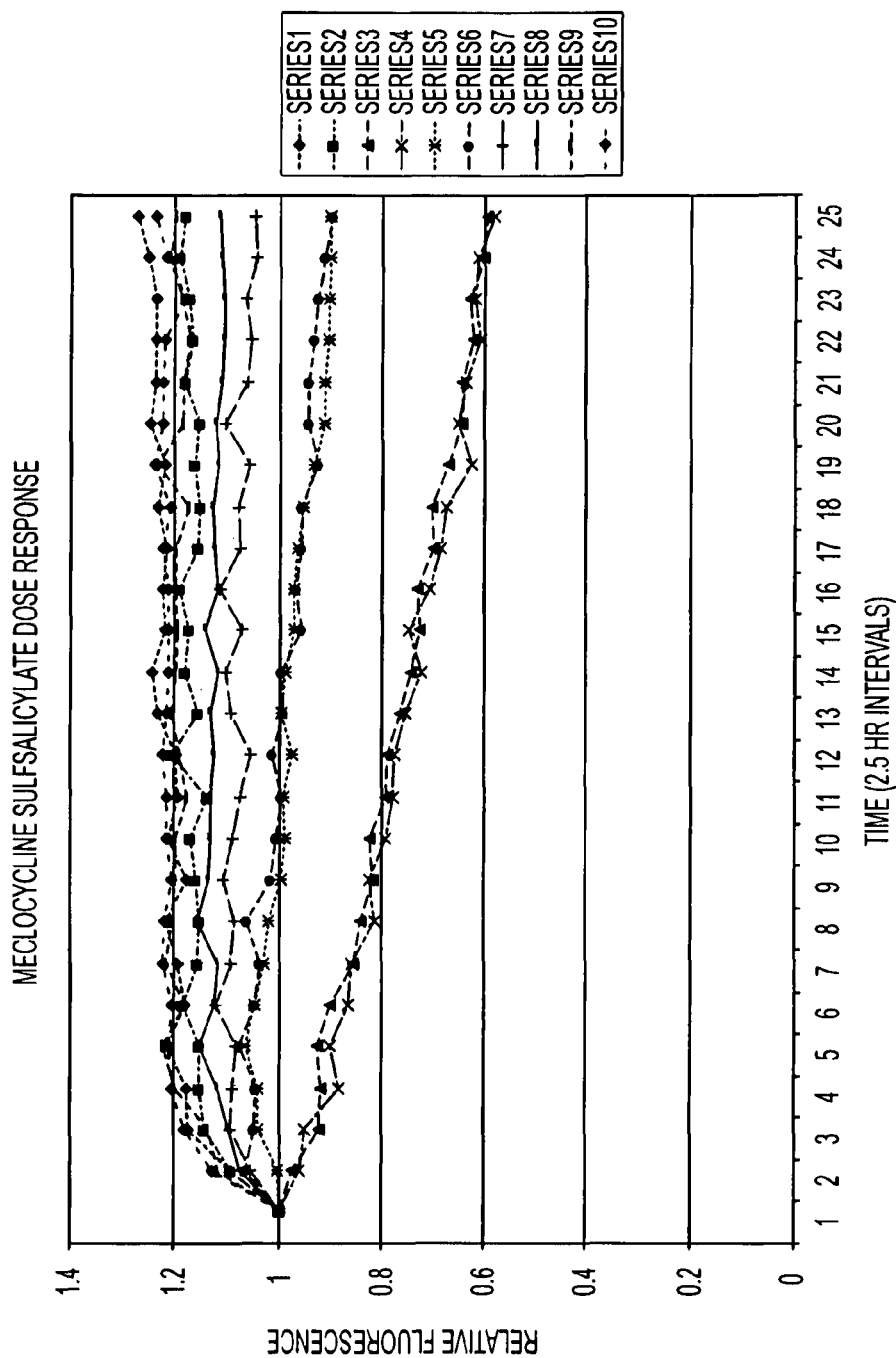
FIG. 8 is a graph depicting the effect of meclocycline sulfosalicylate on the thioflavin T/β-2M fibril fluorescence as a function of time. Meclocycline sulfosalicylate affects the thioflavin T/β-2M fibril fluorescence in a dose-dependent manner at concentrations less than or equal to 10 µM. Series 1 and 2 are duplicate controls (human β-2M fibrils+thioflavin T in 1% DMSO). Series 3 and 4 are duplicates of human β-2M fibrils+thioflavin T+1 mM meclocycline sulfosalicylate (final concentration). Series 5 and 6 are duplicates of human β-2M fibrils+thioflavin T+100 µM meclocycline sulfosalicylate. Series 7 and 8 are duplicates of human β-2M fibrils+thioflavin T+10 µM meclocycline sulfosalicylate. Series 9 and 10 are duplicates of human β-2M fibrils+thioflavin T+1 µM meclocycline sulfosalicylate.
Figure 9:
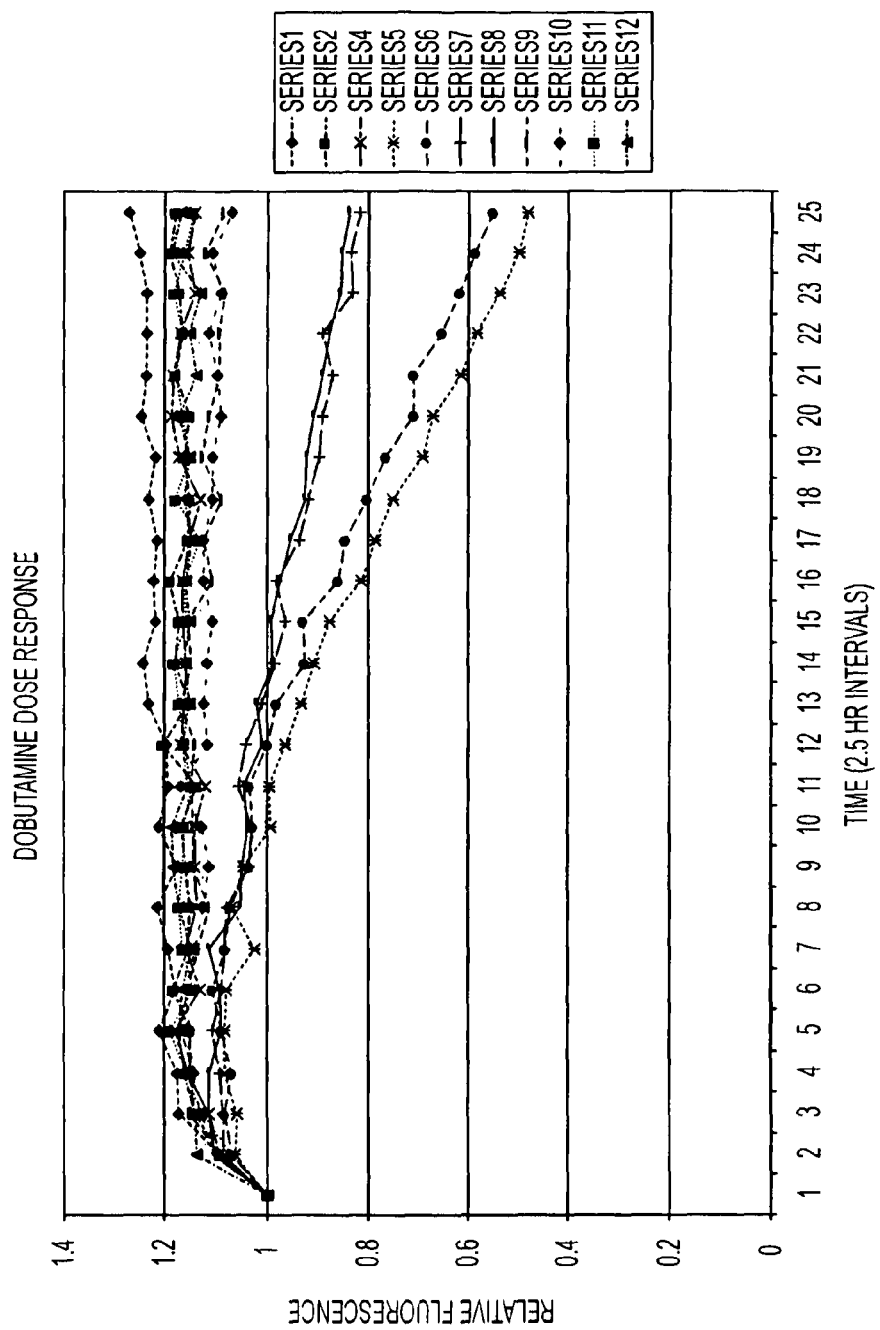
FIG. 9 is a graph depicting the effect of dobutamine hydrochloride on the thioflavin T/β-2M fibril fluorescence as a function of time. Dobutamine hydrochloride affects the thioflavin T/β-2M fibril fluorescence in a dose-dependent manner at concentrations less than or equal to 10 µM. Series 1,2 and 4 are triplicate control samples (human β-2M fibrils+thioflavin T in 1% DMSO). Series 5 and 6 are duplicates of human β-2M fibrils+thioflavin T+1 mM dobutamine hydrochloride (final concentration). Series 7 and 8 are duplicates of human β-2M fibrils+thioflavin T+100 µM dobutamine hydrochloride. Series 9 and 10 are duplicates of human β-2M fibrils+thioflavin T+10 µM dobutamine hydrochloride. Series 11 and 12 are duplicates of human β-2M fibrils+thioflavin T+1 µM dobutamine hydrochloride.
Figure 10:
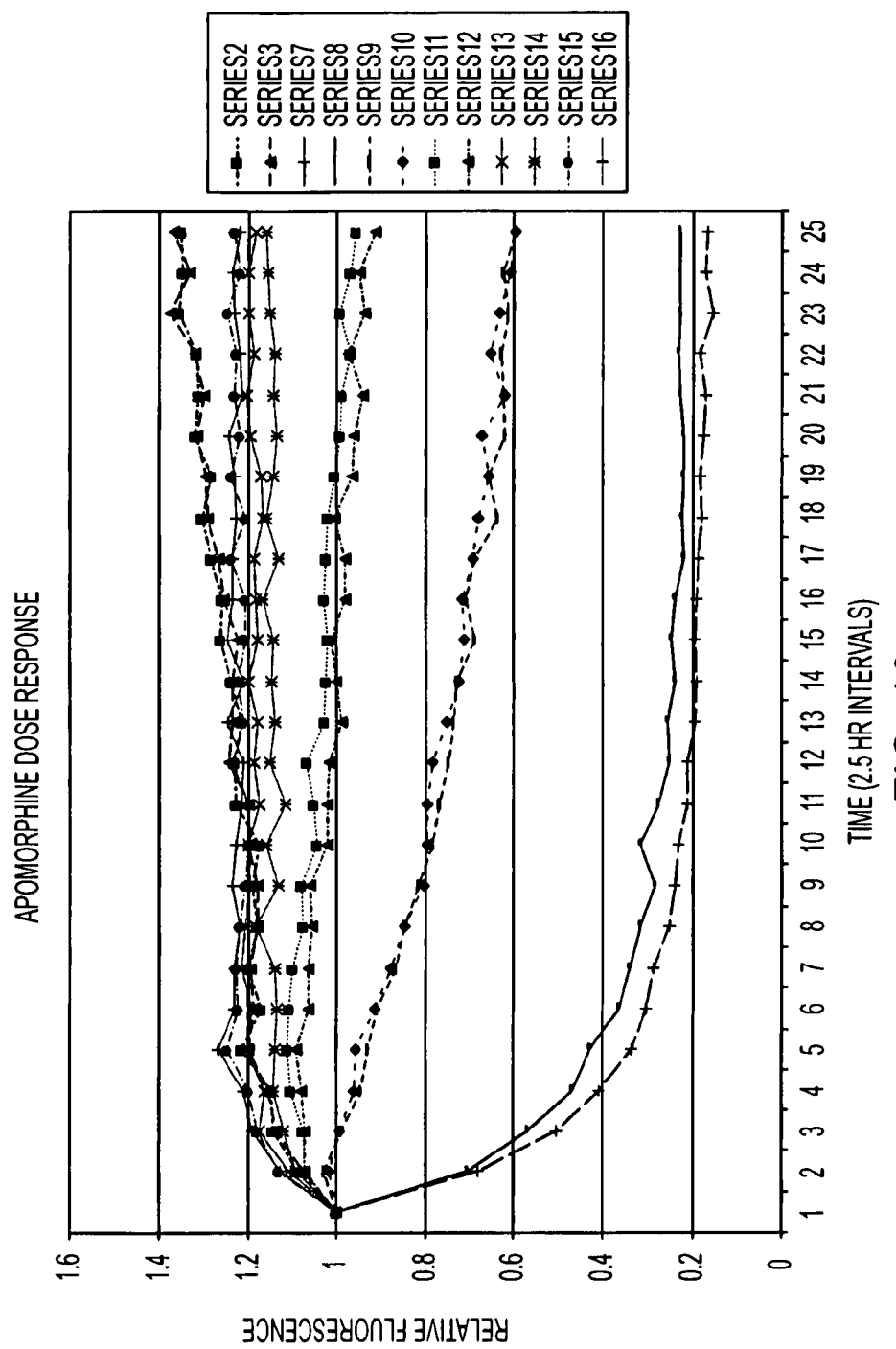
FIG. 10 is a graph depicting the effect of apomorphine hydrochloride on the thioflavin T/β-2M fibril fluorescence as a function of time. Apomorphine hydrochloride affects the thioflavin T/β-2M fibril fluorescence in a dose-dependent manner at concentrations less than or equal to 1 µM. Series 2 and 3 are duplicate control samples (human β-2M fibrils+thioflavin T in water). Series 7 and 8 are duplicates of human β-2M fibrils+thioflavin T+1 mM apomorphine hydrochloride (final concentration). Series 9 and 10 are duplicates of human β-2M fibrils+thioflavin T+100 µM apomorphine hydrochloride. Series 11 and 12 are duplicates of human β-2M fibrils+thioflavin T+10 µM apomorphine hydrochloride. Series 13 and 14 are duplicates of human β-2M fibrils+thioflavin T+1 µM apomorphine hydrochloride. Series 15 and 16 are duplicates of human β-2M fibrils+thioflavin T+100 nM apomorphine hydrochloride.
Figure 11:
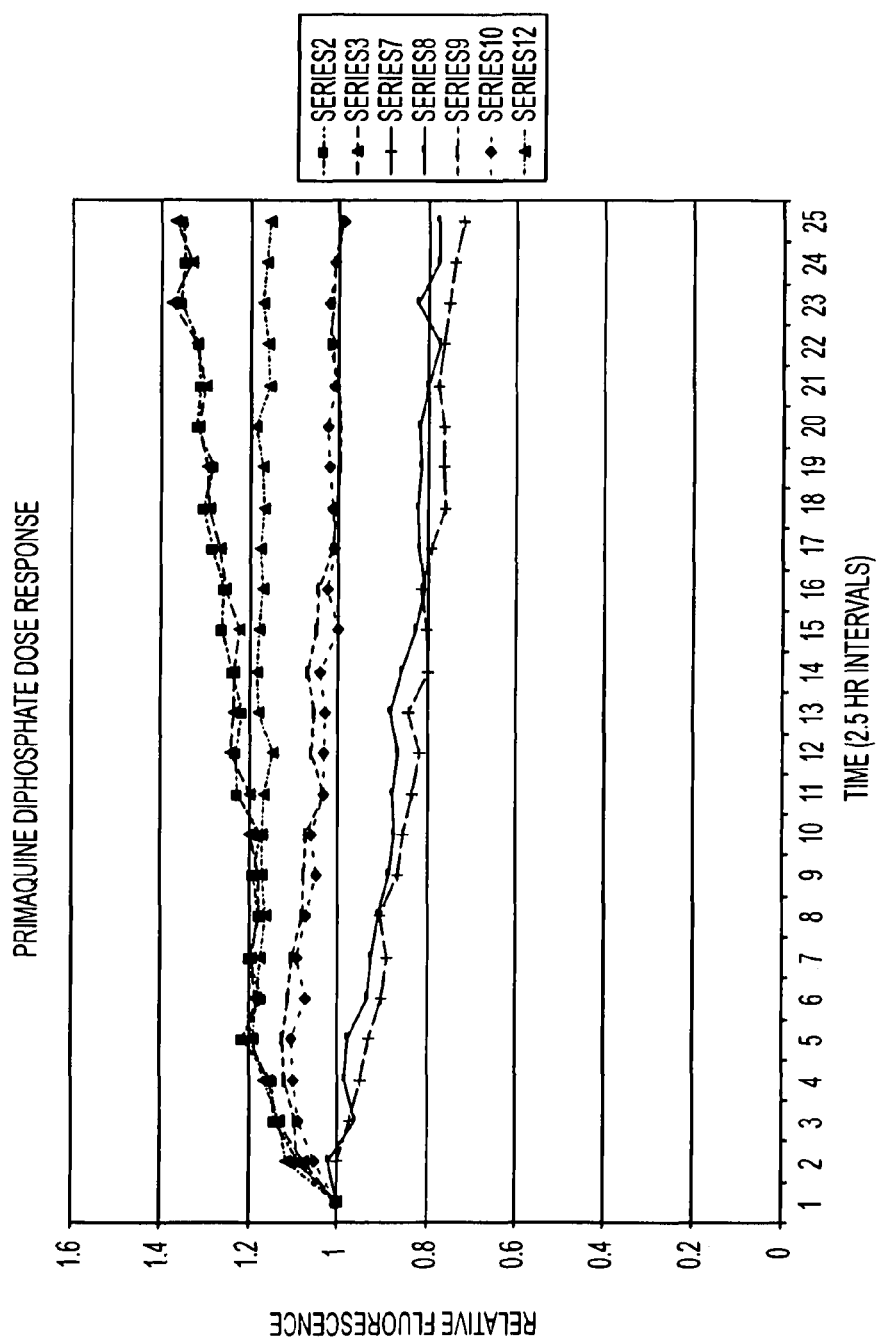
FIG. 11 is a graph depicting the effect of primaquine diphosphate on the thioflavin T/β-2M fibril fluorescence as a function of time. Primaquine diphosphate affects the thioflavin T/β-2M fibril fluorescence in a dose-dependent manner at concentrations less than or equal to 10 µM. Series 2 and 3 are duplicate control samples (human β-2M fibrils+thioflavin T in water). Series 7 and 8 are duplicates of human β-2M fibrils+thioflavin T+1 mM primaquine diphosphate (final concentration). Series 9 and 10 are duplicates of human β-2M fibrils+thioflavin T+100 µM primaquine diphosphate. Series 12 contains human β-2M fibrils+thioflavin T+10 µM primaquine diphosphate
Figure 12A:
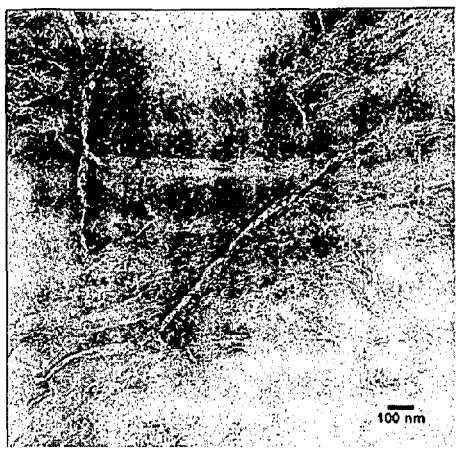
FIGS. 12a to 12c are electron micrographs (EM) demonstrating that haematommic acid disrupts human β2-microglobulin fibrils. Haematommic acid was incubated with preformed human β2-microglobulin fibrils at concentrations of 1 mM and 10 µM. With 1 mM haematommic acid, fibril dissolution was virtually complete after a two-week incubation and the EM field was blank (data not shown). At 10 µM haematommic acid, the fibrils are disrupted and unwound (FIG. 12a) relative to control fibrils (FIGS. 12b and 12c, which present the same view at different magnifications).
Figure 12B:
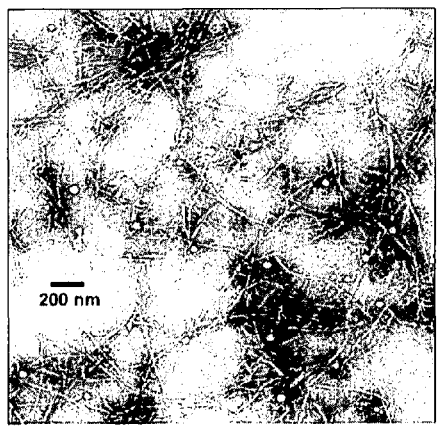
Figure 12C:
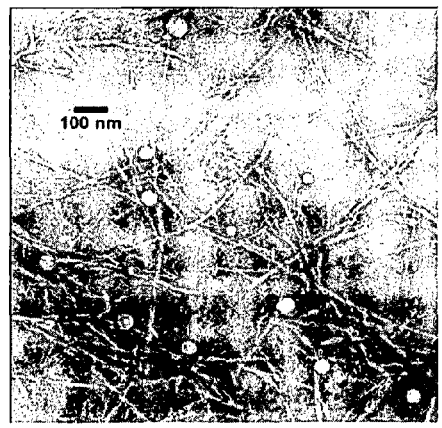
Figure 13:
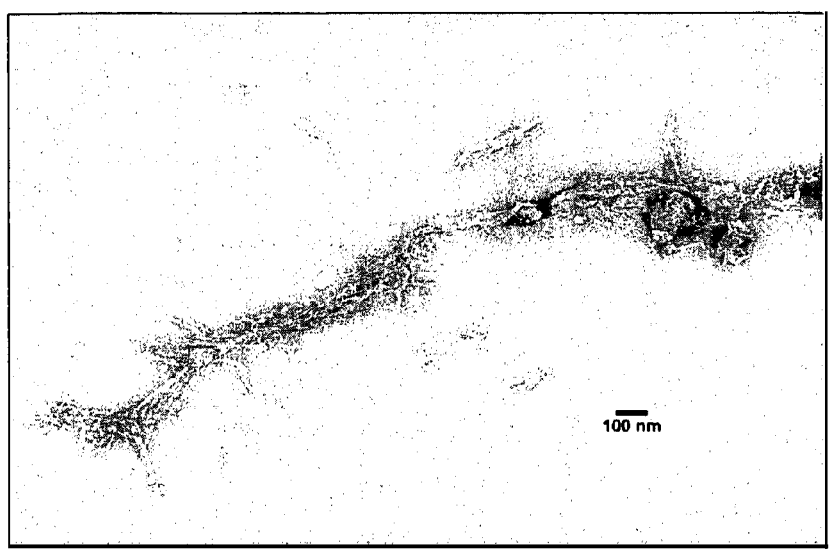
FIG. 13 is an electron micrograph demonstrating that stictic acid disrupts human β2-microglobulin fibrils. Stictic acid was incubated with preformed human β2-microglobulin fibrils at concentrations of 1 mM and 100 μM. After a two-week incubation with 1 mM stictic acid, the fibrils have mostly disappeared with an occasional clumping of disrupted fibrils (see FIG. 13). At 100 μM stictic acid, the fibrils are also mostly disrupted, with the remaining fibrils associating into a sheet-like structure (not shown).
Figure 14A:
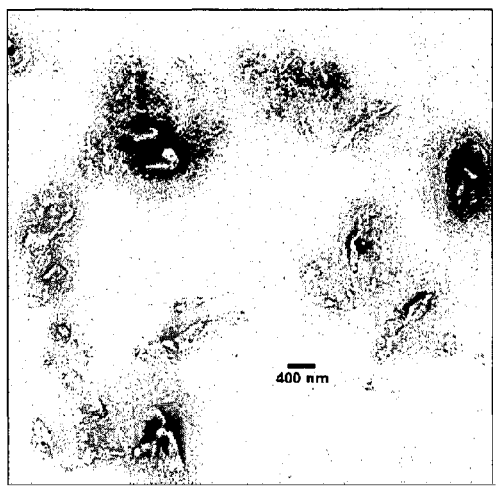
FIGS. 14a to 14c are electron micrographs demonstrating that meclocycline sulfosalicylate disrupts human β2-microglobulin fibrils. Meclocycline sulfosalicylate was incubated with preformed human β2-microglobulin fibrils at concentrations of 1 mM and 100 μM. After a two-week incubation with 1 mM meclocycline sulfosalicylate, there were no visible fibrils (FIG. 14a). At 100 μM meclocycline sulfosalicylate, there are no intact fibrils present (FIGS. 14b and 14c).
Figure 14B:
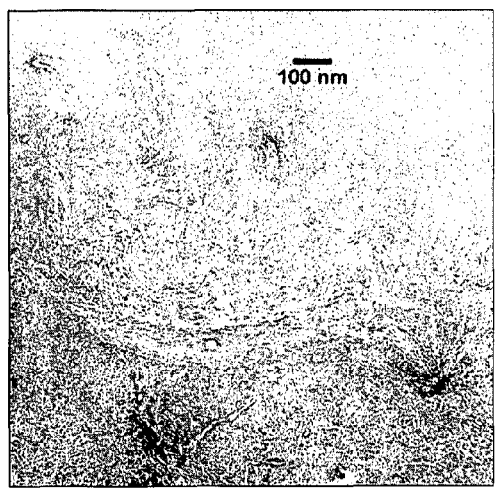
Figure 14C:
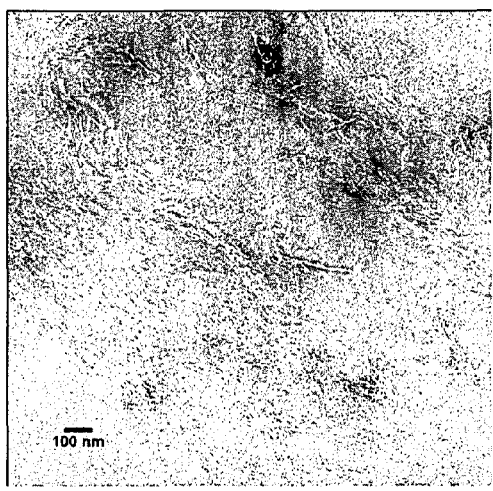

FIG. 5 presents a simple block diagram of a kidney dialysis machine. Blood is taken from the vein of a patient at a blood inflow point 502. The blood then flows into a blood pump 504 which moves the blood through the blood side 510 of the artificial kidney 508, where the blood is purified. The purified blood then is reinjected into a vein of a patient at blood outflow point 506. As the blood passes through the blood side 510 of the artificial kidney 508, the blood is purified because waste substances pass through the semipermeable dialyser membrane 514 into the dialysate side 512 of the artificial kidney 508. Fresh dialysate solution is stored in a fresh dialysate tank 516. The dialysate solution flows into a dialysate pump 518 which moves the dialysate solution through the dialysate side 512 of the artificial kidney 508, where the dialysate solution accumulates waste substances. The dialysate solution containing the waste substances then passes into a waste dialysate tank 520.

The β-2 microglobulin fibril disrupting compound can be combined ex vivo with the blood of a patient in any of several different ways. The β-2 microglobulin fibril disrupting compound can be introduced to the blood upstream of the dialyser membrane 514, that is between the blood inflow point 502 and the blood side 510 of the artificial kidney 508. The β-2 microglobulin fibril disrupting compound can be introduced to the blood downstream of the dialyser membrane 514, that is between the blood side 510 of the artificial kidney 508 and the blood outflow point 506. The β-2 microglobulin fibril disrupting compound can be introduced to the dialysate solution upstream of the dialyser membrane 514, that is into the fresh dialysate tank 516 or between the fresh dialysate tank 516 and the dialysate side 512 of the artificial kidney 508. Alternatively, the β-2 microglobulin fibril disrupting compound can be administered in vitro to the patient.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fine inert powdered carrier and inhaled by the subject or insufflated. Such compositions and preparations may contain at least 0.1% of a compound or compounds of the invention. The percentage of the compositions and preparations may, of course, be varied and may conveniently be between about 2% to about 60% of the weight of a given unit dosage form. The amount of compounds in such therapeutically useful compositions is such that an effective dosage level will be obtained.

The tablets, troches, pills, capsules, and the like may also contain the following: binders such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain the active compound, sucrose or fructose as a sweetening agent, methyl and propylparabens as preservatives, a dye, and flavoring such as cherry or orange flavor. Of course, any material used in preparing any unit dosage form should be pharmaceutically acceptable and substantially non-toxic in the amounts employed. In addition, the compounds of the invention may be incorporated into sustained-release preparations and devices. For example, the compounds may be incorporated into time release capsules, time release tablets, and time release pills.

The compounds of the invention may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. Epigallocatechin gallate and benserazide hydrochloride are soluble in water. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds of the invention may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols or water/alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, lotions, ointments, soaps, and the like, for application directly to the skin of the user.

Useful dosages of the compounds of Formula I can be determined by comparing their in vitro activity, and by comparing their in vivo activity in animal models. Methods for the extrapolation of effective dosages in mice and other animals to humans are known to the art.

For example, the concentration of the compounds in a liquid composition, can be from about 0.1 to about 25% by weight, or from about 0.5 to about 10% by weight. The concentration in a semi-solid or solid composition such as a gel or a powder can be from about 0.1 to about 5% by weight, or from about 0.5 to about 2.5% by weight.

Dosages

The amount of the compounds of the invention required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg per day, e.g., from about 0.01 to about 100 mg/kg of body weight per day, such as from about 0.1 to about 10 mg per kilogram body weight of the recipient per day. For example, a suitable dose may be about 1 mg/kg, 10 mg/kg, or 50 mg/kg of body weight per day.

The compounds of the invention are conveniently administered in unit dosage form; for example, containing from about 0.05 to about 10000 mg, from about 0.5 to about 10000 mg, from about 5 to about 1000 mg, or about 500 mg of active ingredient per unit dosage form.

The compounds of the invention can be administered to achieve peak plasma concentrations of, for example, from about 100 nM to about 10 mM, from about 1 $\mu$M to about 1 mM, or from about 10 $\mu$M to about 100 $\mu$M. Exemplary desirable plasma concentrations include at least or no more than 100 nM, 1 $\mu$M, 10 $\mu$M, 100 $\mu$M, 1 mM, or 10 mM. This may be achieved, for example, by the intravenous injection of a 0.05 to 5% solution of the compounds of the present invention, optionally in saline, or orally administered as a bolus containing about 1-1000 mg of the compounds. Desirable blood levels may be maintained by continuous infusion to provide from about 0.00005 to about 5 mg per kg body weight per hour, for example at least or no more than 0.00005, 0.0005, 0.005, 0.05, 0.5, or 5 mg/kg/hr. Alternatively, such levels can be obtained by intermittent infusions containing from about 0.0002 to about 20 mg per kg body weight, for example, at least or no more than 0.0002, 0.002, 0.02, 0.2, 2, 20, or 50 mg of the compounds per kg of body weight.

The compounds of the invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLE 1

Preparation of Human β-2 Microglobulin Fibrils

The human β-2 microglobulin fibrils were prepared in vitro at 0.1 mg/mL protein in 25 mM phosphate, pH 2, 0.2 M NaCl without agitation for 1 week at 37° C., in the same manner as Ivanova et al. See Ivanova et al. (*Proc Natl Acad Sci U.S.A.* 2004 Jul. 20; 101(29):10584-9).

EXAMPLE 2

Thioflavin T Fluorescence Assay for Detecting the Presence of Amyloid Fibrils

In our experiments, disruption of the fibrillar structure of preformed β-2 microglobulin fibrils was monitored by fluorescence. The dye used, thioflavin T, serves as a probe for the presence or absence of amyloid fibrils. Thioflavin T binds specifically to human β-2 microglobulin fibrils, causing a red shift in the fluorescence excitation spectra of the dye to produce a peak in the fluorescence emission spectrum at 482 nm when the excitation wavelength is set at 444 nm. Nonfibrillar β-2 microglobulin does not cause such a red shift (FIG. 1) (LeVine, H. 1999 *Methods in Enzymology;*

309:274-84.). Because aliquoting of fibrils has an inherent variability, we aimed for a high signal/noise ratio of ~10. FIG. 1 shows that this ratio is sufficient to distinguish fibrillar and nonfibrillar samples.

β-2 microglobulin fibrils prepared in vitro retain the characteristic amyloid properties, including binding ThT. In the fluorescence assay used here, preformed human β-2 microglobulin fibrils were mixed with a solution of 5 μM ThT in 50 mM glycine, pH 8.6 in a 3:14 ratio (final concentrations: 4.1 μM ThT, 41.2 mM glycine, 0.018 mg/mL β-2 microglobulin, 35 mM NaCl and 4.4 mM phosphate). Fluorescence was measured immediately after mixing (excitation wavelength set at 444 nm, emission wavelengths at 482, 490, and 502 nm) with a Molecular Devices FlexStation II. Using 50 μL/well of this solution produced a fluorescence signal that was, on average, 10 times the fluorescence intensity of the control sample (control sample is nonfibrillar β-2 microglobulin prepared in the same manner, but freshly disrupted and not incubated at 37° C., then mixed with 5 μM ThT in 50 mM glycine pH 8.6, in the same ratios as the fibrillar samples).

EXAMPLE 3

High Throughput Screening

In our experiments, we screened 5200 compounds to determine whether a compound could disrupt preformed human β-2 microglobulin fibrils. Preformed β-2 microglobulin fibrils and ThT were mixed in the ratios described above in Example 2 and divided among seventeen 384-well glass-bottom plates (Costar #6569) using 40 μL/well. Each of the sixteen commercial plates contained four columns of control wells: columns 1, 2, and 23 contained preformed fibrils+dimethylsulfoxide (herein, DMSO), but no compound; column 24 contained nonfibrillar β2M+DMSO (no compound). The final concentrations of compound and DMSO in the other wells were 10 μM and 1%, respectively. Compounds were obtained from the following chemical libraries: the MicroSource Discovery Systems, Inc. Spectrum Collection library (*J Virology* 77: 10288 (2003); *Ann Rev Med* 56: 321 (2005)), the first four plates from the Prestwick Chemical Inc. library, two BIOMOL plates (phosphatase/kinase inhibitor library and bioactive lipid library), and the first five plates from the ChemBridge Corporation DIVERSet.

Plate 17 was prepared in-house and set up slightly differently than the commercial plates. Column 24 contains nonfibrillar B2M as in the other plates. However, only the first two rows contain added compounds, and the remaining rows contain control samples (fibrils mixed with thioflavin T, no compound). The chemicals used to prepare this supplemental plate were purchased from SIGMA. For each compound, a 1 mM solution in OmniSolv DMSO was prepared and filtered with Millex-FG 0.2 micron filters. The supplementary plate contained compounds at 1 or 10 mM in 100% DMSO, such that the final screening concentration is 10 or 100 μM compound in 1% DMSO.

All plates were read manually on a Molecular Devices FlexStation II using the bottom-read function. For each of the wells, an initial fluorescence intensity measurement was taken as a baseline. Immediately after adding library compounds to the wells, another fluorescence measurement was made. Subsequent readings were taken at 1 hr, day 1, day 2, day 3, day 4, day 7, day 9 and every few days thereafter for one month. Plates were sealed and stored in darkness between readings.

Figure 2A:
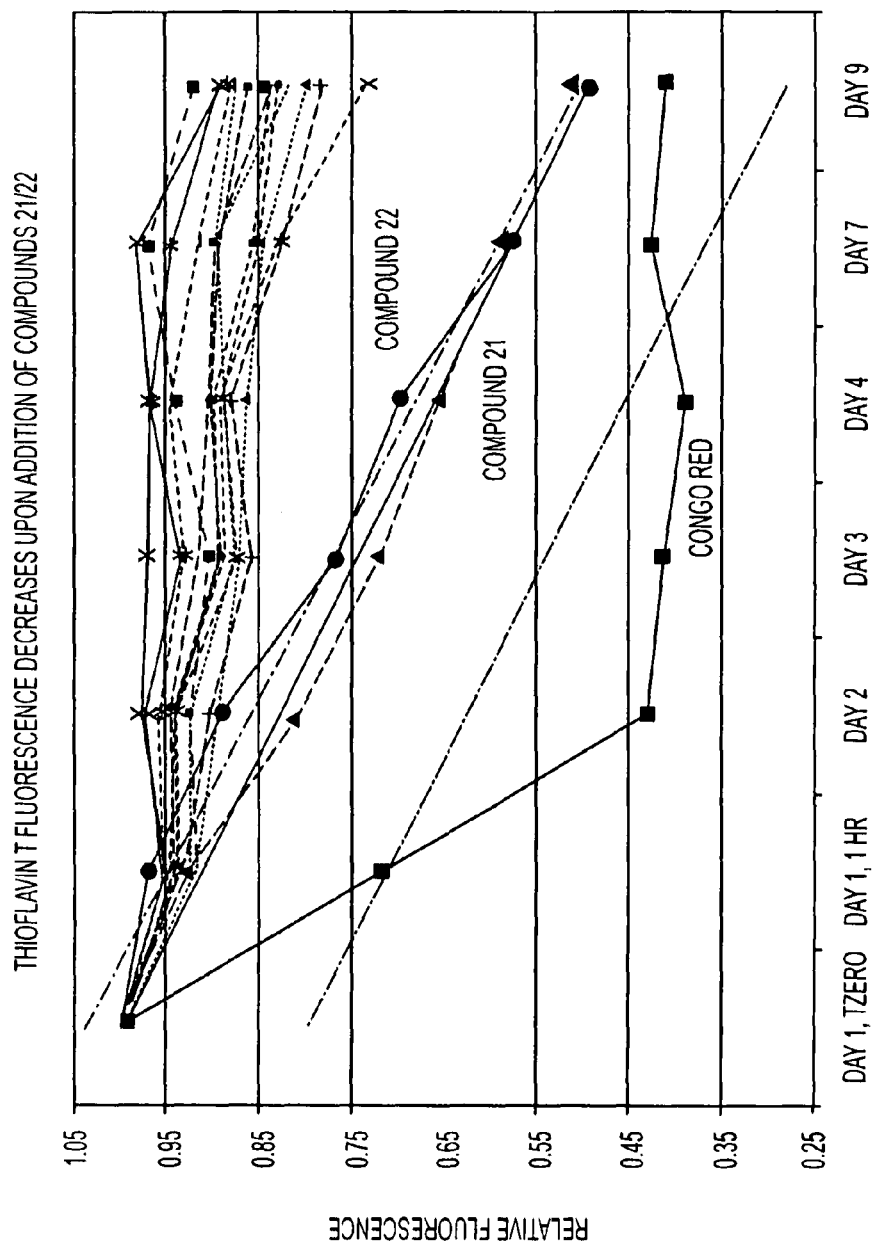
FIG. 2*a* is a graph depicting the relative fluorescence of thioflavin T as a function of time. Each thioflavin T fluorescence curve represents a single compound added to human B2M fibrils. The curves shown in the figure represent one row of a 384-well plate. The control sample with no added compound is represented by the curve in the upper cluster. Three curves observed upon the addition of compounds that significantly decrease the B2M-ThT fluorescence (Congo red, compound 21, and compound 22) are shown. Solid black or alternating dot-dash lines that lack data point symbols are linear regressions. There is one linear regression associated with each of the compound 21, compound 22, and congo red curves.
Figure 2B:
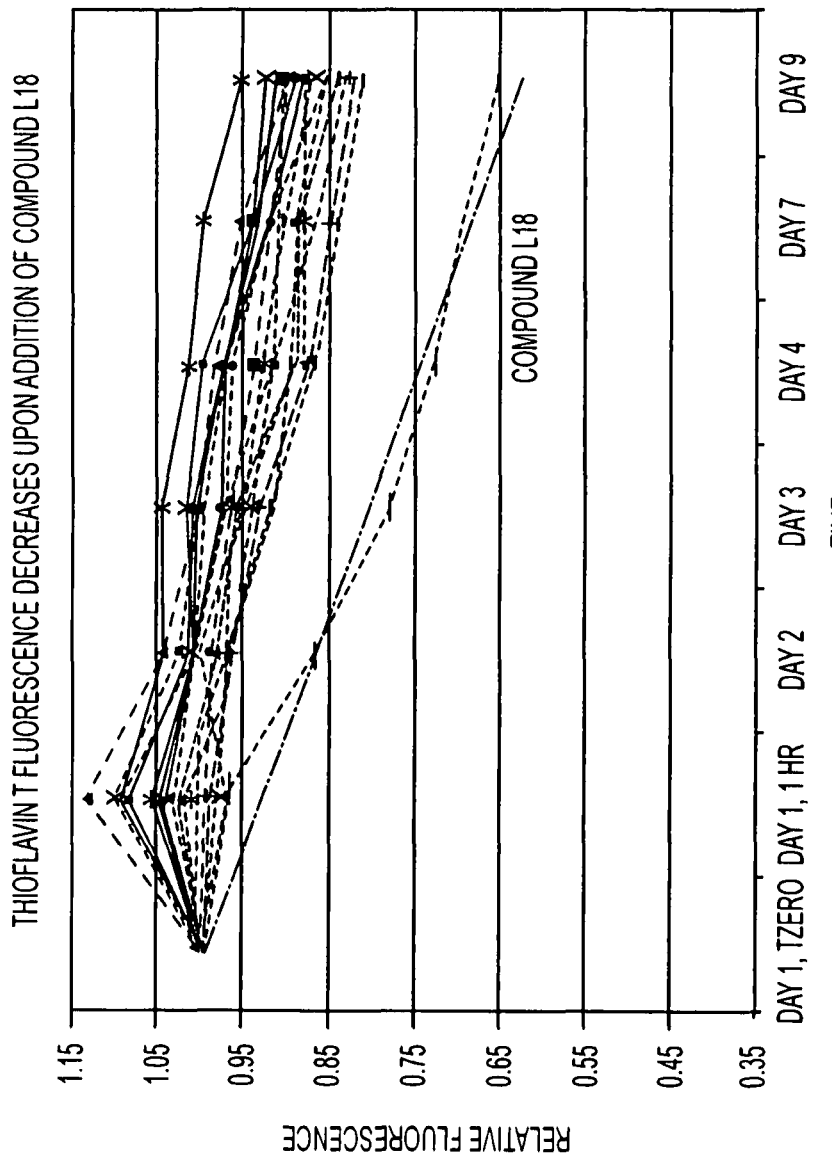
FIG. 2*b* is a graph depicting the relative fluorescence of thioflavin T as a function of time. Each thioflavin T fluorescence curve represents a single compound added to human B2M fibrils. The curves shown in FIG. 2*b* represent one row of a 384-well plate (a different row than is depicted in FIG. 2*a*). The control sample with no added compound is represented by a curve in the upper cluster. One curve observed upon the addition of compound that significantly decreased the B2M-ThT fluorescence (compound L18) is shown. The alternating dot-dash line that lacks data point symbols is a linear regression. There is a linear regression associated with the L18 curve.
Figure 2C:
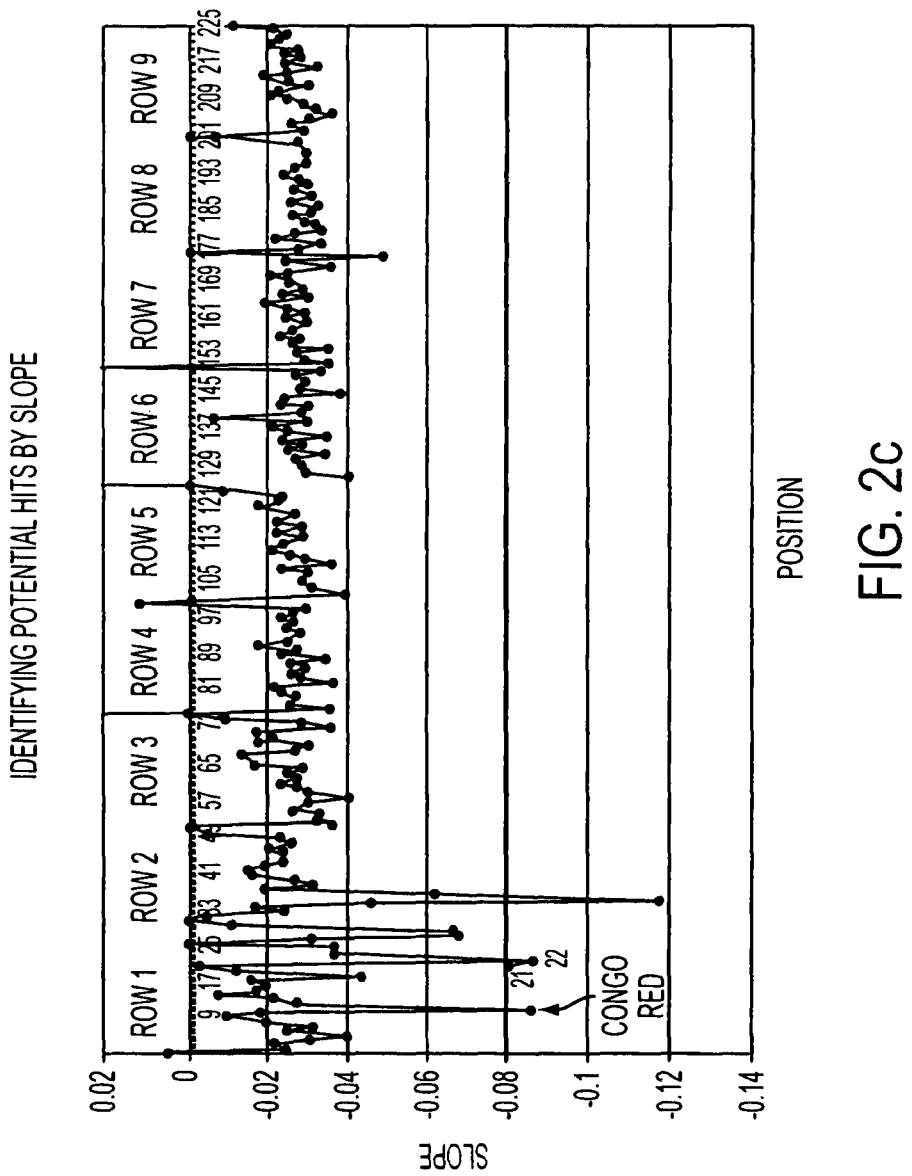
FIG. 2c is a graph in which points depict the slope of the thioflavin T versus time curve for wells in a 384-well plate. The red line represents the slope threshold that was used to identify potential hits. Only 9 rows of a single 384-well plate are shown, thus not all potential hits are presented in this figure.

For each well, a plot of fluorescence intensity versus time was made (FIG. 2). These plots were normalized to the first data point after compound was added (to avoid following compounds that quench the fluorescence), and a linear regression was performed. Compounds that disrupted the human β-2 microglobulin fibrils, that is, the amyloid fibril structure, decreased the measured fluorescence intensity of thioflavin T over time relative to controls. Compounds that disrupted the fibrils generally produced a slow, continuous drop in fluorescence over time. The compounds were ranked according to slope, with the most negative slope receiving the highest score. Using a slope threshold of −0.08 (FIG. 2c) and eliminating fluorescent compounds, we identified four hits that were commercially available. Additionally, we chose three compounds with scores in the −0.06 to −0.07 range that were structurally or functionally related to those four hits. The seven compounds are gabapentin, benserazide, quercetin, EGCG, valproate, resveratrol-3-glucoside, and perphenazine. Dose-response tests were performed on the seven compounds: benserazide and EGCG yielded dose-related effects on fluorescence. The compounds EGCG, benserazide, valproate, and resveratrol-3-glucoside were tested by electron microscopy: benserazide and EGCG had an effect on fibrils; valproate and resveratrol-3-glucoside did not have an effect on fibrils. Thus, the dose-response tests correlate with the electron microscopy results.

Additionally, the compounds apomorphine hydrochloride, primaquine diphosphate, haematommic acid, stictic acid, dobutamine hydrochloride were selected as potential hits because they had slopes in the −0.06- to −0.07 range and were either structurally related to one of the first seven hits or were duplicated in the screen and shown to have a slope effect in duplicate. Compounds with slopes in the range of about −0.06 are also potential hits. The best compounds were retested.

EXAMPLE 4

Dose-Response Testing

Twelve compounds were selected for testing their dose-response effects. Dose-response curves were derived as follows. Preformed β-2 microglobulin fibrils were mixed with ThT in the ratios described above and divided into portions of 40 μL per well across 8 wells. The final concentrations were the same as used in the high-throughput screen: 4.1 μM ThT, 41.2 mM glycine, 0.018 mg/mL B2M, 35 mM NaCl, 4.4 mM phosphate. The first and last wells of each row were controls (B2M fibrils+ThT+solvent (water or DMSO)). To wells 2-7 of a given row, test compound was added to the β2M fibril/ThT mix such that the following final concentrations in the well were reached: 10 mM, 1 mM, 100 μM, 10 μM, 1 μM, and 100 nM. Each row was set up in duplicate. The wells were incubated for 99 hours and data collected at 2.5 hour intervals. Compound 22 was tested using both water and DMSO as solvent.

Figure 3A:
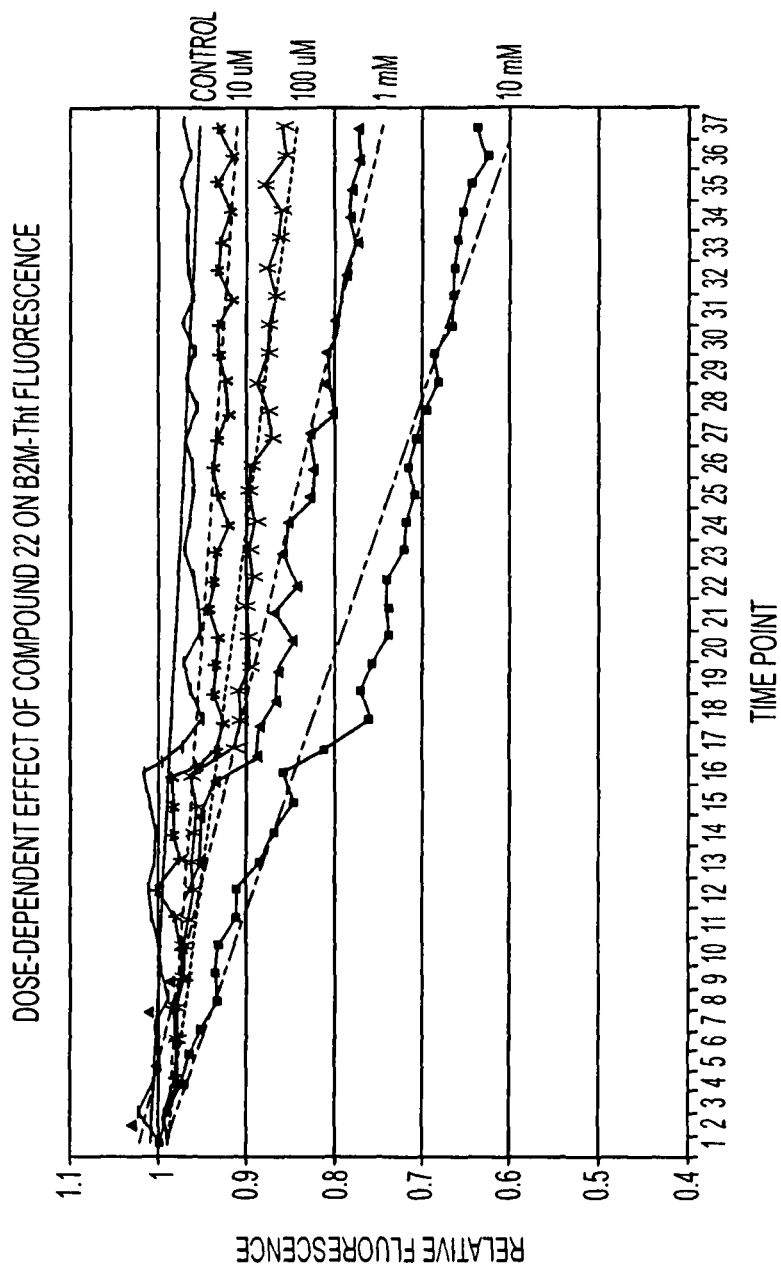
FIG. 3a is a graph depicting the relative fluorescence of thioflavin T as a function of time. Each curve represents a different dose of compound 22 added to human B2M fibrils. The more negative the slope, the stronger the effect on fluorescence. Curves are shown for a control, in which no compound was added, and for samples to which 10 µM, 100 µM, 1 mM, and 10 mM were respectively added. The solid, dashed or alternating dot-dash lines that lack data point symbols are linear regressions. There is a linear regression associated with each dose-response curve.
Figure 3B:
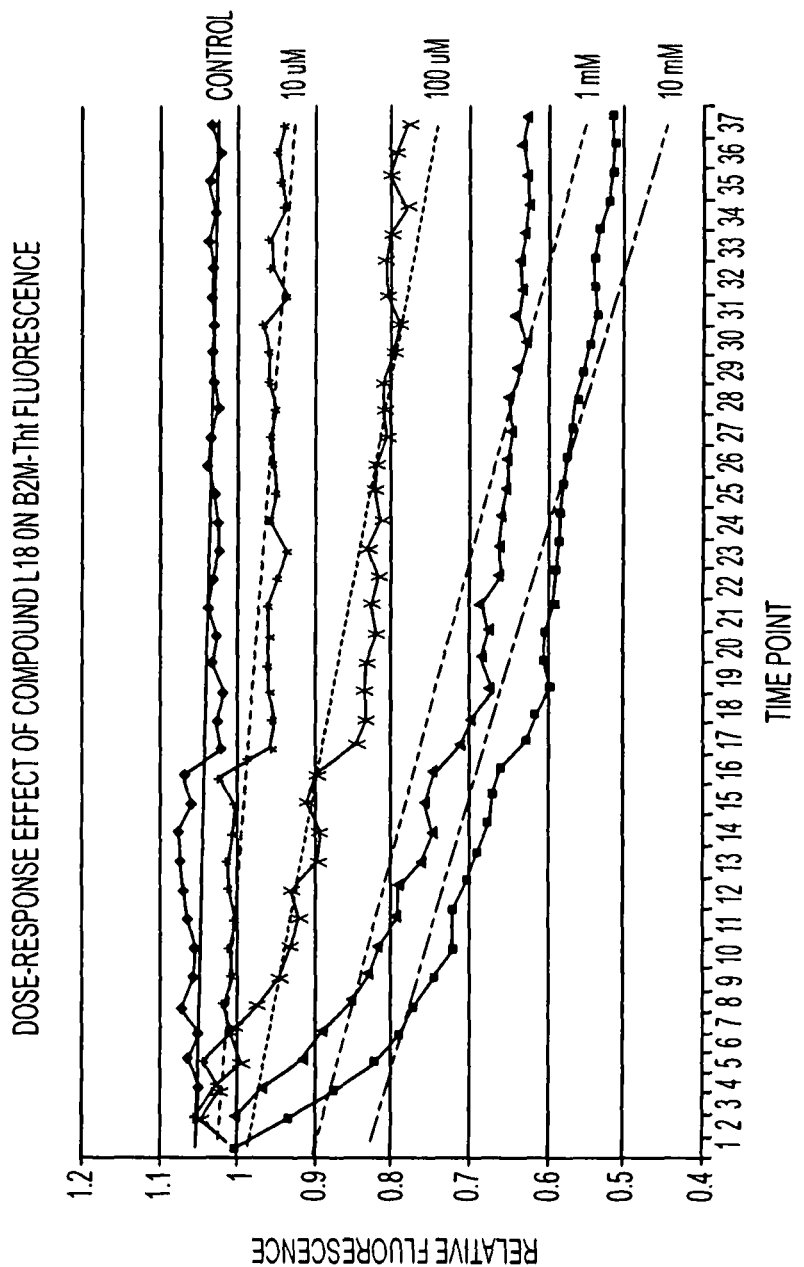
FIG. 3b is a graph depicting the relative fluorescence of thioflavin T as a function of time. Each curve represents a different dose of compound L18 added to human B2M fibrils. The more negative the slope, the stronger the effect on fluorescence. Curves are shown for a control, in which no compound was added, and for samples to which 10 µM, 100 µM, 1 mM, and 10 mM were respectively added. The solid, dashed or alternating dot-dash lines that lack data point symbols are linear regressions. There is a linear regression associated with each dose-response curve.
Figure 4A:
FIG. 4a is an electron micrograph showing the presence of human B2M fibrils incubated at room temperature for 14 days with no added compound.
Figure 4B:
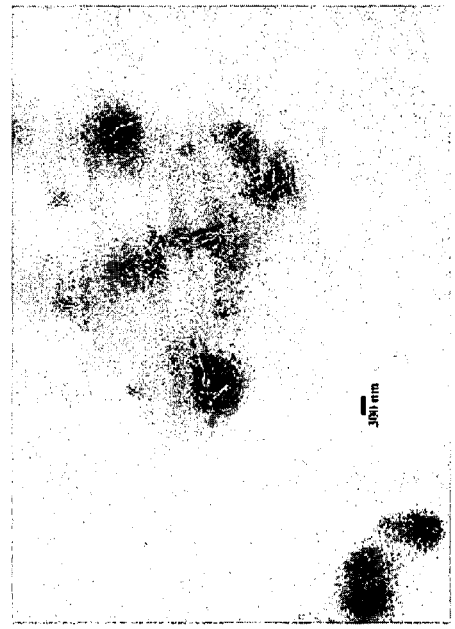
FIG. 4b is an electron micrograph showing a zoomed-out view of human B2M fibrils incubated at room temperature for 14 days with 1 mM Compound 22 added. A bar indicating a distance of 300 nm is shown.
Figure 4C:
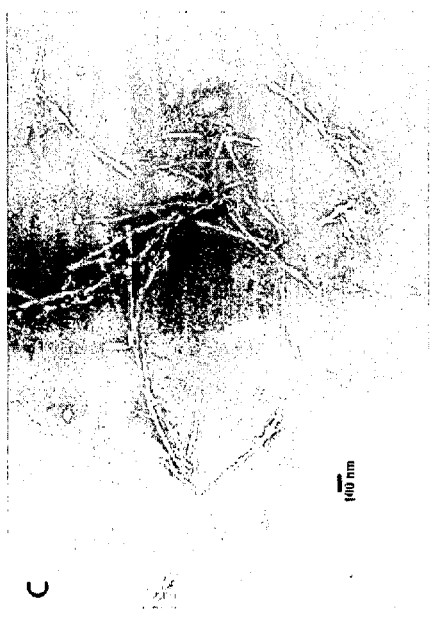
FIG. 4c is an electron micrograph showing a zoomed-in view of the image presented in FIG. 4b. A bar indicating a distance of 100 nm is shown.
Figure 4D:
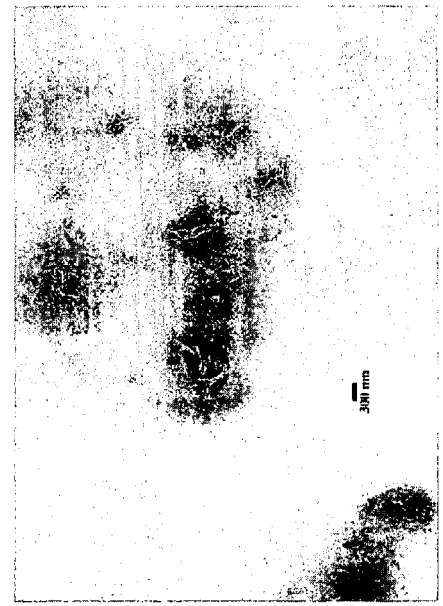
FIG. 4d is an electron micrograph showing a zoomed-out view of human B2M fibrils incubated at room temperature for 14 days with 10 µM compound 22 added.

The dose-response curves for compounds 22 and L18 are shown in FIG. 3. It is visually apparent that concentrations down to 10 μM of both compound 22 and L18 affect the B2M/Tht fluorescence.

To confirm that the decrease in fluorescence intensity was due to disruption of fibrillar structure, for the compounds that gave the best dose-response curves (i.e., those compounds for which an effect was observed with the least amount of compound), electron microscopy was used as a secondary assay to check the state of fibrillar structure over time.

EXAMPLE 5

Electron Microscopy as a Secondary Screen

Electron microscopy was used to confirm the effects of, among others, compounds 22 and L18 on the fibrils. Compounds 22 and L18 were mixed with drug and solvent or solvent alone and were separately incubated with preformed human β-2 microglobulin fibrils for two weeks. Compound 22 was tested at three concentrations (1 mM, 100 μM, and 10 μM). Aliquots were taken immediately after mixing, at day 2, at day 5, day 7, and day 14. Samples were fixed to grids (made hydrophilic by glow-discharge) upon taking the aliquots, washed with distilled water, and stained with 1% uranyl acetate. Grids were examined in a Hitachi H-7000 transmission electron microscope operating at 75 kV. Images were collected on Kodak electron microscope film 4489.

FIG. 4 shows the effect of compound 22 on the fibrils after two weeks. By day 14 almost all of the fibrils in the 1 mM Compound 22 sample had been disrupted and the field had to be searched to find any fibril remnants (shown in panel b). In the 10 μM sample, the fibrils are also significantly disrupted (panel d).

EXAMPLE 6

Compounds useful for Treating β-2 Microglobulin Aggregation in Dialysis-Related Amyloidosis

TABLE 1

| Compound | Molecular Structure | Slope Assay Score | Dose-Response (conc. at which slope is better than control) | Disaggregates β2M fibrils as observed by EM (+/−) |
|---|---|---|---|---|
| Epigallocatechin Gallate (EGCG) | | −.087 | 10 μM | + |
| Stictic Acid | 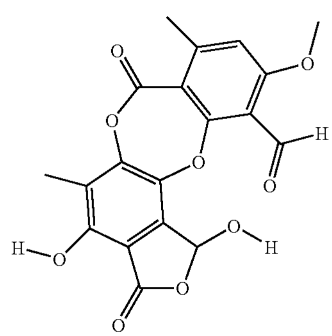 [SMILES: COc1cc(C)c2c(c1C=O)Oc1c(c(C)c(O)c3c1C(O)OC3=O)OC2=O] | −.098 | 10 μM | + |

TABLE 1-continued

| Compound | Molecular Structure | Slope Assay Score | Dose-Response (conc. at which slope is better than control) | Disaggregates β2M fibrils as observed by EM (+/−) |
|---|---|---|---|---|
| Haematommic Acid | 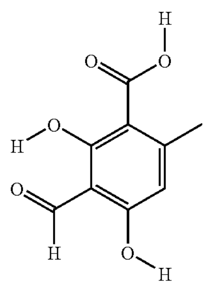 | −.076 | 1 μM | + |
| Benserazide hydrochloride | 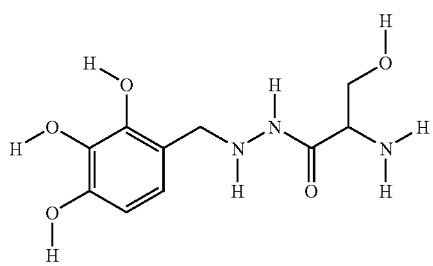 [SMILES: NC(CO)C(=O)NNCc1ccc(O)c(O)c1O] | −.066 | 10 μM | + |
| Meclocycline sulfosalicylate | | −.066 | 10 μM | + |
| Apomorphine hydrochloride hemihydrate | 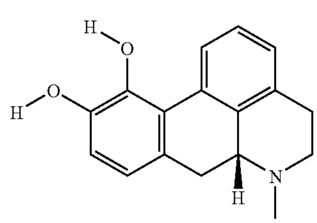 [SMILES: CN1CCc2cccc3c2[C@H]1Cc1ccc(O)c(O)c1-3] | −.061 | 1-10 μM | N/A |

TABLE 1-continued

| Compound | Molecular Structure | Slope Assay Score | Dose-Response (conc. at which slope is better than control) | Disaggregates β2M fibrils as observed by EM (+/−) |
|---|---|---|---|---|
| Dobutamine hydrochloride | 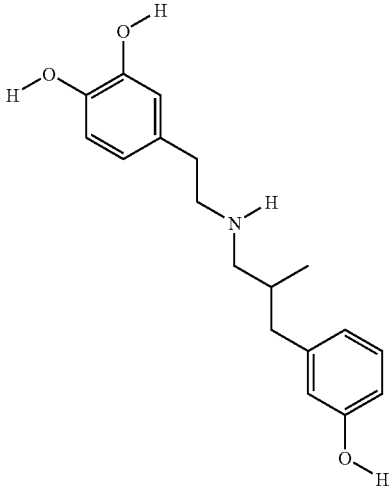 [SMILES: CC(CNCCc1ccc(O)c(O)c1)Cc1cccc(O)c1] | −.058 | 10 µM | N/A |
| Primaquine diphosphate | 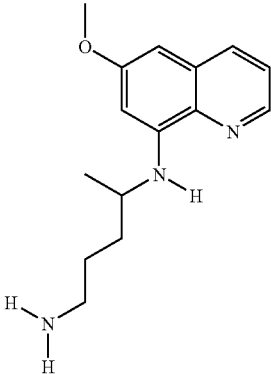 [SMILES: COc1cc(NC(C)CCCN)c2ncccc2c1] | −.058 | 10 µM | N/A |

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

"Neuroprotective effects of green and black teas and their catechin gallate esters against beta-amyloid-induced toxicity" Bastianetto et al., (*Eur J Neurosci*. (2006) January; 23(1):55-64.)

"Green tea consumption and cognitive function: a cross-sectional study from the Tsurugaya Project" Kuriyama et al., (*Am J Clin Nutr* (2006) February;83(2):355-61.)

"Preformed beta-amyloid fibrils are destabilized by coenzyme Q10 in vitro."(this article describes the ability of Coenzyme Q 10 and a wine-related polyphenol, myricetin, to disrupt preformed amyloid fibrils). Ono et al., (*Biochem Biophys Res Commun*. (2005) April 29;330(1): 111-6.)

Abe, T., K. Uchita, et al. (2003). "Effect of beta(2)-microglobulin adsorption column on dialysis-related amyloidosis." *Kidney Int* 64(4): 1522-8.

Ayli, M., D. Ayli, et al. (2005). "The effect of high-flux hemodialysis on dialysis-associated amyloidosis." *Ren Fail* 27(1): 31-4.

Ivanova, M. I., M. R. Sawaya, et al. (2004). "An amyloid-forming segment of beta2-microglobulin suggests a molecular model for the fibril." *Proc Natl Acad Sci U S A* 101(29): 10584-9.

Jadoul, M. (1998). "Dialysis-related amyloidosis: importance of biocompatibility and age." *Nephrol Dial Transplant* 13 Supp 7: 61-4.

LeVine, H., 3rd (1999). "Quantification of beta-sheet amyloid fibril structures with thioflavin T." *Methods Enzymol* 309: 274-84.

Pepys, M. B. (2006). "Amyloidosis." *Annu Rev Med* 57: 223-41.

Tsuruoka, S., M. Wakaumi, et al. (2004). "Beta2-microglobulin adsorption column reduces digoxin trough level during. hemodialysis: three case reports." *Ther Drug Monit* 26(4): 450-2.

Winchester, J. F., J. A. Salsberg, et al. (2003). "Beta-2 microglobulin in ESRD: an in-depth review." *Adv Ren Replace Ther* 10(4): 279-309.

Yamamoto, S. and F. Gejyo (2005). "Historical background and clinical treatment of dialysis-related amyloidosis." *Biochim Biophys Acta* 1753(1): 4-10.

What is claimed is:

1. A dialysis system comprising an upstream blood side, an artificial kidney, and a downstream blood side, and benserazide hydrochloride, stictic acid, haemmatommic acid, meclocycline sulfosalicylate, dobutamine hydrochloride, apomorphine hydrochloride or primaquine diphosphate.

2. The dialysis system of claim 1, wherein the system comprises benserazide hydrochloride.

3. The dialysis system of claim 1, wherein the system comprises stictic acid.

4. The dialysis system of claim 1, wherein the system comprises haemmatommic acid.

5. The dialysis system of claim 1, wherein the system comprises meclocycline sulfosalicylate.

6. The dialysis system of claim 1, wherein the system comprises dobutamine hydrochloride.

7. The dialysis system of claim 1, wherein the system comprises apomorphine hydrochloride.

8. The dialysis system of claim 1, wherein the system comprises primaquine diphosphate.

9. A method for treating dialysis-related amyloidosis in a subject comprising combining blood of the subject with a β-2 microglobulin fibril disrupting compound selected from the group consisting of one or more of benserazide hydrochloride, stictic acid, haemmatommic acid, meclocycline sulfosalicylate, dobutamine hydrochloride, apomorphine hydrochloride, and primaquine diphosphate, wherein the β-2 microglobulin fibril disrupting compound is combined ex vivo with the blood during dialysis treatment of the subject.

10. The method of claim 9, wherein the β-2 microglobulin fibril disrupting compound comprises benserazide hydrochloride.

11. The method of claim 9, wherein the β-2 microglobulin fibril disrupting compound comprises stictic acid.

12. The method of claim 9, wherein the β-2 microglobulin fibril disrupting compound comprises haemmatommic acid.

13. The method of claim 9, wherein the β-2 microglobulin fibril disrupting compound comprises meclocycline sulfosalicylate.

14. The method of claim 9, wherein the β-2 microglobulin fibril disrupting compound comprises dobutamine hydrochloride.

15. The method of claim 9, wherein the β-2 microglobulin fibril disrupting compound comprises apomorphine hydrochloride.

16. The method of claim 9, wherein the β-2 microglobulin fibril disrupting compound comprises primaquine diphosphate.

* * * * *